US009629517B2

(12) United States Patent
Sakai et al.

(10) Patent No.: US 9,629,517 B2
(45) Date of Patent: *Apr. 25, 2017

(54) SCANNING ENDOSCOPE SYSTEM

(71) Applicant: OLYMPUS CORPORATION, Tokyo (JP)

(72) Inventors: Yuji Sakai, Kodaira (JP); Yoshinari Okita, Hachioji (JP)

(73) Assignee: OLYMPUS CORPORATION, Tokyo (JP)

(*) Notice: Subject to any disclaimer, the term of this patent is extended or adjusted under 35 U.S.C. 154(b) by 297 days.

This patent is subject to a terminal disclaimer.

(21) Appl. No.: 14/269,297

(22) Filed: May 5, 2014

(65) Prior Publication Data
US 2015/0038786 A1 Feb. 5, 2015

Related U.S. Application Data

(63) Continuation of application No. PCT/JP2013/074102, filed on Sep. 6, 2013.

(30) Foreign Application Priority Data

Oct. 22, 2012 (JP) ................ 2012-233024

(51) Int. Cl.
A61B 6/00 (2006.01)
A61B 1/00 (2006.01)
(Continued)

(52) U.S. Cl.
CPC ...... A61B 1/00098 (2013.01); A61B 1/00013 (2013.01); A61B 1/00165 (2013.01);
(Continued)

(58) Field of Classification Search
CPC ............ A61B 1/00098; A61B 1/00172; A61B 1/00181; A61B 1/00183; A61B 90/361;
(Continued)

(56) References Cited

U.S. PATENT DOCUMENTS 7,129,472 B1 10/2006 Okawa et al.
2008/0218824 A1 9/2008 Johnston et al.
(Continued)

FOREIGN PATENT DOCUMENTS

EP 1 142 529 A1 10/2001
JP 2010-148764 A 7/2010
(Continued)

OTHER PUBLICATIONS

Karpelson, Michael, Gu-Yeon Wei, and Robert J. Wood. "Driving High Voltage Piezoelectric Actuators in Microrobotic Applications." Driving High Voltage Piezoelectric Actuators in Microrobotic Applications. Elsevier B.V., Jan. 8, 2012. Web. Jul. 27, 2016. Publication:Sensors and Actuators A 176 (2012) 78-89.*
Extended Supplementary European Search Report dated Jan. 29, 2016 from related European Application No. 13 84 9728.4.

Primary Examiner — Ryan Henderson
Assistant Examiner — Pamela Wu
(74) Attorney, Agent, or Firm — Scully, Scott, Murphy & Presser, P.C.

(57) ABSTRACT

A scanning endoscope system includes: a fiber that guides illuminating light emitted from a light source; a first actuator provided on a side of the fiber, the first actuator expanding/contracting according to an applied voltage, thereby swinging the fiber; a second actuator disposed at a position facing the first actuator across the fiber, the second actuator expanding/contracting according to an applied voltage, thereby swinging the fiber; and a drive signal output section that applies a first drive signal that varies with reference to a first voltage that brings the first actuator into a contracted state to the first actuator and applies a second drive signal that varies with reference to a second voltage that brings the second actuator into a contracted state to the second actuator.

6 Claims, 3 Drawing Sheets

(51) Int. Cl.
*G02B 23/26* (2006.01)
*A61B 1/07* (2006.01)
*G02B 23/24* (2006.01)
*G02B 26/10* (2006.01)
*A61B 1/04* (2006.01)

(52) U.S. Cl.
CPC ............ *A61B 1/00172* (2013.01); *A61B 1/07* (2013.01); *G02B 23/2469* (2013.01); *G02B 23/26* (2013.01); *G02B 26/103* (2013.01); *A61B 1/042* (2013.01)

(58) Field of Classification Search
CPC ...... A61B 2090/3614; A61B 2090/373; A61B 1/0053; A61B 1/0058; A61B 1/0607; A61B 1/00057; A61B 1/00059; A61B 1/00006; A61B 1/0062; A61B 1/0064; A61B 1/0066; G02B 26/103
USPC .................................................. 600/152, 143
See application file for complete search history.

(56) References Cited

U.S. PATENT DOCUMENTS

| | | |
|---|---|---|
| 2008/0265178 A1 | 10/2008 | Johnston |
| 2009/0028407 A1 | 1/2009 | Seibel et al. |
| 2009/0219384 A1* | 9/2009 | Iketani ................. A61B 1/0638 348/45 |
| 2010/0168515 A1* | 7/2010 | Sugimoto ............ A61B 1/0008 600/109 |
| 2013/0242069 A1* | 9/2013 | Kobayashi ......... A61B 1/00009 348/65 |

FOREIGN PATENT DOCUMENTS

| | | |
|---|---|---|
| JP | 2010-527028 A | 8/2010 |
| JP | 2011-115252 A | 6/2011 |
| JP | 2012-110479 A | 6/2012 |
| JP | 2012-152244 A | 8/2012 |
| WO | WO 2008133636 A1 | 11/2008 |
| WO | WO 2012070298 A1 | 5/2012 |

* cited by examiner

US 9,629,517 B2

SCANNING ENDOSCOPE SYSTEM

CROSS REFERENCE TO RELATED APPLICATION

This application is a continuation application of PCT/JP2013/074102 filed on Sep. 6, 2013 and claims benefit of Japanese Application No. 2012-233024 filed in Japan on Oct. 22, 2012, the entire contents of which are incorporated herein by this reference.

BACKGROUND OF THE INVENTION

1. Field of the Invention

The present invention relates to a scanning endoscope system, and specifically relates to a scanning endoscope system for scanning an object to obtain an image.

2. Description of the Related Art

In endoscopes in a medical field, in order to reduce a burden on subjects, various techniques for thinning insertion portions to be inserted into body cavities of the subjects have been proposed. As an example of such techniques, a scanning endoscope including no solid image pickup device in a part corresponding to the aforementioned insertion portion and a system including the scanning endoscope are known.

More specifically, the system including the scanning endoscope is configured to, for example, swing a distal end portion of an illumination fiber that guides illuminating light emitted from a light source section to two-dimensionally scan an object according to a pre-set scanning pattern, receive return light from the object via light-reception fibers disposed in the periphery of the illumination fiber and generate an image of the object based on the return light received via the light-reception fibers. As an example of those having a configuration similar to such system, the scanning beam system disclosed in U.S. Patent Application Publication No. 2008/0218824 is known.

SUMMARY OF THE INVENTION

A scanning endoscope system comprising: a fiber configured to guide illuminating light emitted from a light source; a first actuator disposed on a side of the fiber, wherein the first actuator is configured to deform by expanding and contracting upon application of an applied voltage according to a first drive signal, thereby swinging the fiber; a second actuator disposed at a position facing the first actuator across the fiber, wherein the second actuator is configured to deform by expanding and contracting upon application of an applied voltage according to a second drive signal, thereby swinging the fiber; a drive signal output section configured to output the first drive signal and the second drive signal, wherein the first actuator and the second actuator are configured to deform in opposite directions when a polarity of the first drive signal and a polarity of the second drive signal are the same; and a controller configured to control the drive signal output section to: generate the first drive signal varying with a first voltage as a center, and set the first voltage larger than zero, generate the second drive signal varying with a second voltage as a center, and set the second voltage smaller than zero, and align a phase of the first drive signal and the second drive signal.

DETAILED DESCRIPTION OF THE PREFERRED EMBODIMENT

An embodiment of the present invention will be described below with reference to the drawings.

Figure 1:
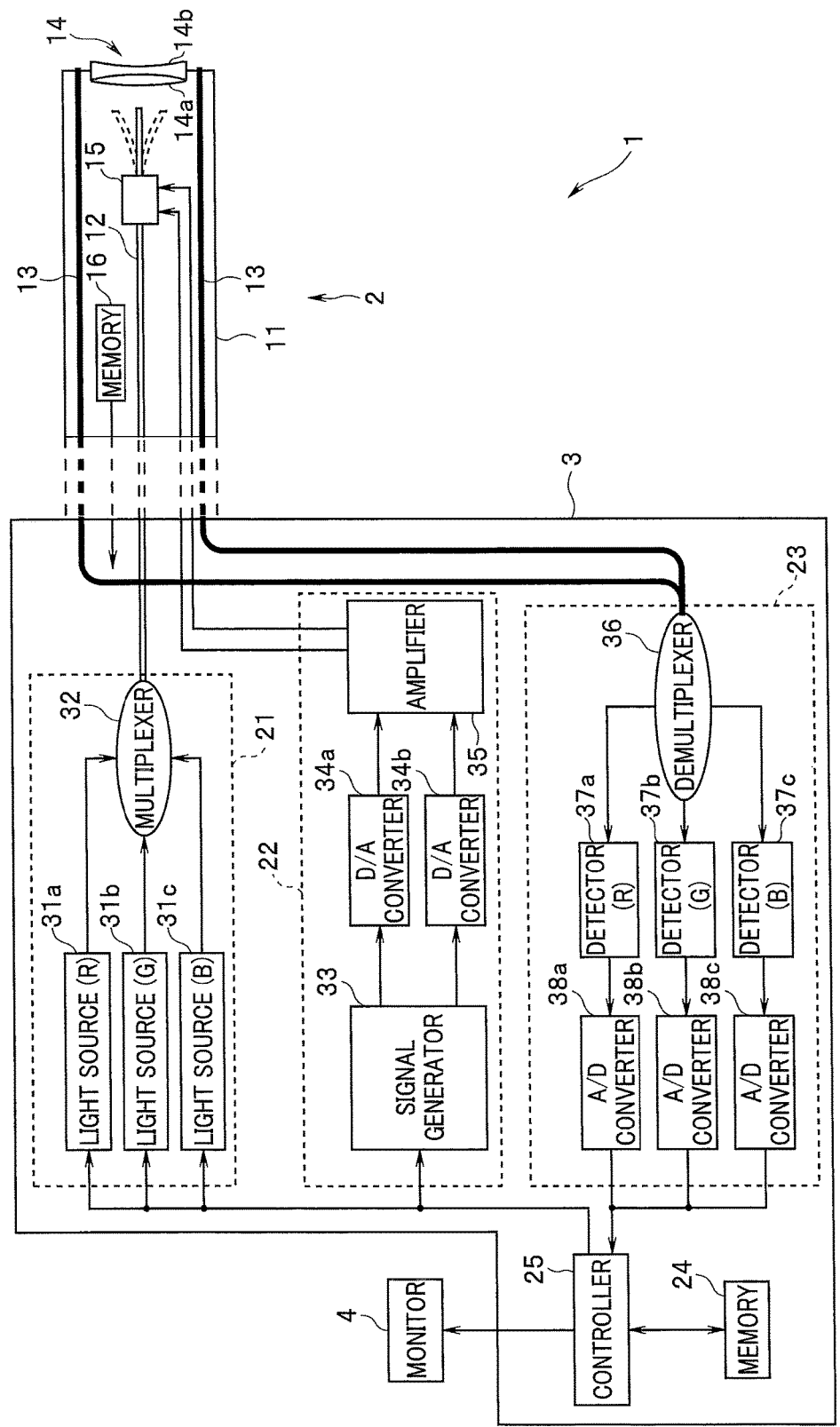
FIG. 1 is a diagram illustrating a configuration of a main part of a scanning endoscope system according to an embodiment.

FIGS. 1 to 4 relate to an embodiment of the present invention. FIG. 1 is a diagram illustrating a configuration of a main part of a scanning endoscope system according to the embodiment.

A scanning endoscope system 1 includes, for example, as illustrated in FIG. 1, a scanning endoscope 2 to be inserted into a body cavity of a subject, a body apparatus 3 to be connected to the scanning endoscope 2 and a monitor 4 to be connected to the body apparatus 3.

The scanning endoscope 2 includes an insertion portion 11 formed so as to have an elongated shape and flexibility that enable the insertion portion 11 to be inserted into a body cavity of a subject. Note that in a proximal end portion of the insertion portion 11, e.g., a non-illustrated connector for connecting the scanning endoscope 2 to the body apparatus 3 and disconnecting the scanning endoscope 2 from the body apparatus 3 is provided.

In a part from the proximal end portion to a distal end portion of the inside of the insertion portion 11, an illumination fiber 12 having a function as a light-guiding section that guides illuminating light supplied from a light source unit 21 of the body apparatus 3 to a light collection optical system 14, and light-reception fibers 13 that receive return light from an object and guide the return light to a detection unit 23 of the body apparatus 3 are inserted, respectively.

An end portion of the illumination fiber 12 that includes a light entrance surface is disposed in a multiplexer 32 provided inside the body apparatus 3. Also, an end portion of the illumination fiber 12 that includes a light exit surface is disposed in the vicinity of a light entrance surface of a lens 14a provided in the distal end portion of the insertion portion 11 in such a manner that the end portion is not fixed via, e.g., a fixing member.

An end portion of each light-reception fiber 13 that includes a light entrance surface is fixedly disposed in the periphery of a light exit surface of a lens 14b in a distal end face of the distal end portion of the insertion portion 11. Also, an end portion of each light-reception fiber 13 that includes a light exit surface is disposed in a demultiplexer 36 provided inside the body apparatus 3.

The light collection optical system 14 includes the lens 14a and the lens 14b, and is configured to collect illuminating light entered from the illumination fiber 12 and make the resulting illuminating light exit to the object.

In a portion partway of the illumination fiber 12 on the distal end portion side of the insertion portion 11, an actuator section 15 that is driven based on drive signals outputted from a driver unit 22 of the body apparatus 3 is provided.

Figure 2:
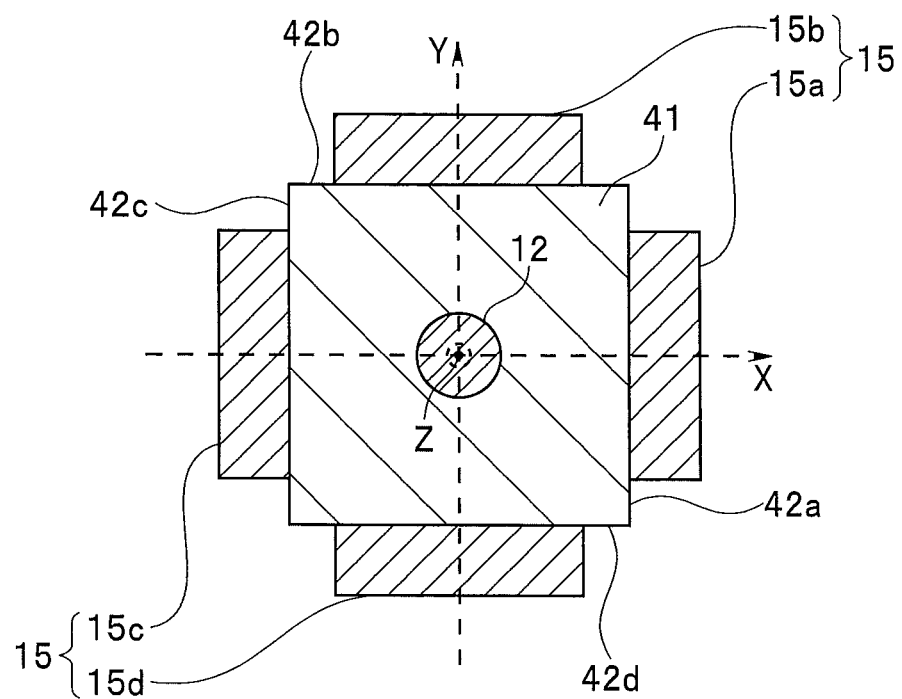
FIG. 2 is a cross-sectional diagram for describing a configuration of an actuator section provided in the scanning endoscope.

The illumination fiber 12 and the actuator section 15 are each disposed so as to have, for example, the positional relationship illustrated in FIG. 2 in a cross-section perpendicular to a longitudinal axis direction of the insertion portion 11. FIG. 2 is a cross-sectional diagram for describing a configuration of the actuator section provided in the scanning endoscope.

As illustrated in FIG. 2, a ferrule 41, which serves as a joining member, is disposed between the illumination fiber 12 and the actuator section 15. More specifically, the ferrule 41 is formed of, for example, zirconia (ceramic) or nickel.

As illustrated in FIG. 2, the ferrule 41 is formed in the shape of a quadrangular prism, and includes side faces 42a and 42c perpendicular to an X-axis direction (transverse direction in the sheet) and side faces 42b and 42d perpendicular to a Y-axis direction (vertical direction in the sheet). Also, at a center of the ferrule 41, the illumination fiber 12 is fixedly disposed. Note that the ferrule 41 may be formed in another shape other than a quadrangular prism as long as such shape is a prism.

As illustrated in FIG. 2, the actuator section 15 includes an actuator 15a disposed along the side face 42a, an actuator 15b disposed along the side face 42b, an actuator 15c disposed along the side face 42c and an actuator 15d disposed along the side face 42d.

In other words, the actuator section 15, which has a function as an optical scanning section, includes a pair of actuators 15a and 15c disposed at respective positions that face the Y-axis (or are symmetrical with respect to the Y-axis) across the illumination fiber 12, along the X-axis direction, and a pair of actuators 15b and 15d disposed at respective positions that face the X-axis (or are symmetrical with respect to the X-axis) across the illumination fiber 12, along the Y-axis direction.

Each of the actuators 15a, 15b, 15c and 15d is configured to be driven according to a drive signal outputted from the driver unit 22.

The actuator 15a includes, for example, a piezoelectric element subjected to polarization processing in advance so that a polarization direction thereof agrees with a negative direction of the X-axis (direction from the right to the left in the sheet of FIG. 2), and is configured to, upon application of a voltage of a positive value according to a drive signal outputted from the driver unit 22 (if a direction of an electric field generated as a result of supply of the drive signal is a forward direction relative to the polarization direction), contract along a Z-axis direction (normal direction in the sheet), and upon application of a voltage of a negative value according to a drive signal outputted from the driver unit 22 (if a direction of an electric field generated as a result of supply of the drive signal is a backward direction relative to the polarization direction), expand along the Z-axis direction.

The actuator 15b includes, for example, a piezoelectric element subjected to polarization processing in advance so that a polarization direction thereof agrees with a negative direction of the Y-axis (direction from the top to the bottom in the sheet of FIG. 2), and is configured to, upon application of a voltage of a positive value according to a drive signal outputted from the driver unit 22, contract along the Z-axis direction, and upon application of a voltage of a negative value according to a drive signal outputted from the driver unit 22, expand along the Z-axis direction.

The actuator 15c includes, for example, a piezoelectric element subjected to polarization processing in advance so that a polarization direction thereof agrees with the negative direction of the X-axis, and is configured to, upon application of a voltage of a negative value according to a drive signal outputted from the driver unit 22, contract along the Z-axis direction, and upon application of a voltage of a positive value according to a drive signal outputted from the driver unit 22, expand along the Z-axis direction.

The actuator 15d includes, for example, a piezoelectric element subjected to polarization processing in advance so that a polarization direction thereof agrees with the negative direction of the Y-axis, and is configured to, upon application of a voltage of a negative value according to a drive signal outputted from the driver unit 22, contract in the Z-axis direction, and upon application of a voltage of a positive value according to a drive signal outputted from the driver unit 22, expand along the Z-axis direction.

Note that according to the present embodiment, the actuator section 15 is not limited to one configured using the actuators 15a to 15d having such polarization directions and expansion/contraction directions as described above, and may be configured using actuators 15a to 15d having other polarization directions and expansion/contraction directions.

Inside the insertion portion 11, a memory 16 with endoscope information stored in advance, the endoscope information including various pieces of information such as individual identification information for the scanning endoscope 2, is provided. Upon the scanning endoscope 2 and the body apparatus 3 being connected, the endoscope information stored in the memory 16 is read from a controller 25 in the body apparatus 3.

The body apparatus 3 includes the light source unit 21, the driver unit 22, the detection unit 23, a memory 24 and the controller 25.

The light source unit 21 includes a light source 31a, a light source 31b, a light source 31c and the multiplexer 32.

The light source 31a includes, for example, a laser light source, and is configured to, when the light source 31a is controlled to be turned on by the controller 25, emit light of a red wavelength band (hereinafter also referred to as "R light") to the multiplexer 32.

The light source 31b includes, for example, a laser light source, and is configured to, when the light source 31b is controlled to be turned on by the controller 25, emit light of a green wavelength band (hereinafter also referred to as "G light") to the multiplexer 32.

The light source 31c includes, for example, a laser light source, and is configured to, when the light source 31c is controlled to be turned on by the controller 25, emit light of a blue wavelength band (hereinafter referred to as "B light") to the multiplexer 32.

The multiplexer 32 is configured to combine the R light emitted from the light source 31a, the G light emitted from the light source 31b, and the B light emitted from the light source 31c and supply the resulting light to the light entrance surface of the illumination fiber 12.

The driver unit 22 has a function as a drive signal output section, and includes a signal generator 33, D/A converters 34a and 34b, and an amplifier 35.

The signal generator 33 is configured to generate respective drive signals for swinging the end portion of the illumination fiber 12 that includes the light exit surface, based on control performed by the controller 25, and output the respective drive signals to the D/A converters 34a and 34b.

The D/A converters 34a and 34b are configured to convert the respective digital drive signals outputted from the signal generator 33 into analog drive signals and output the analog drive signals to the amplifier 35.

The amplifier 35 is configured to amplify the respective drive signals outputted from the D/A converters 34a and 34b and output the resulting drive signals to the actuator section 15.

The detection unit 23 includes the demultiplexer 36, detectors 37a, 37b and 37c, and A/D converters 38a, 38b and 38c.

The demultiplexer 36 includes, e.g., a dichroic mirror, and is configured to split return light that has exited from the light exit surfaces of the light-reception fibers 13 into light of R (red) components, light of G (green) components and light of B (blue) components and make the light of R (red) components, the light of G (green) components and the light of B (blue) components exit to the respective detectors 37a, 37b and 37c.

The detector 37a is configured to detect an intensity of the R light outputted from the demultiplexer 36, generate an analog R signal according to the detected intensity of the R light and output the analog R signal to the A/D converter 38a.

The detector 37b is configured to detect an intensity of the G light outputted from the demultiplexer 36, generate an analog G signal according the detected intensity of the G light and output the analog G signal to the A/D converter 38b.

The detector 37c is configured to detect an intensity of the B light outputted from the demultiplexer 36, generate an analog B signal according to the detected intensity of the B light and output the analog B signal to the A/D converter 38c.

The A/D converter 38a is configured to convert the analog R signal outputted from the detector 37a into a digital R signal and output the digital R signal to the controller 25.

The A/D converter 38b is configured to convert the analog G signal outputted from the detector 37b into a digital G signal and output the digital G signal to the controller 25.

The A/D converter 38c is configured to convert the analog B signal outputted from the detector 37c into a digital B signal and output the digital B signal to the controller 25.

In the memory 24, e.g., a control program for performing control of the body apparatus 3 is stored in advance. Also, in the memory 24, endoscope information read by the controller 25 in the body apparatus 3 is stored.

The controller 25 includes, e.g., a CPU, and is configured to read the control program stored in the memory 24, and perform control of the light source unit 21 and the driver unit 22 based on the read control program. In other words, the actuator section 15, which has a function as an optical scanning section, can swing the illumination fiber 12 so that positions of illuminating light on an object illuminated by the illuminating light form a trajectory according to a predetermined scanning pattern, based on drive signals outputted from the driver unit 22 according to control performed by the controller 25 such as described above.

The controller 25 operates so as to store the endoscope information outputted from the memory 16 when the insertion portion 11 is connected to the body apparatus 3, in the memory 24.

The controller 25 is configured to generate an image based on the R signal, the G signal and the B signal outputted from the detection unit 23, and display the generated image on the monitor 4.

Next, an operation, etc., of the scanning endoscope system 1 having the above described configuration will be described.

When power sources of the respective components of the scanning endoscope system 1 are turned on, the endoscope information stored in the memory 16 in the insertion portion 11 is read by the controller 25, and the read endoscope information is stored in the memory 24.

The controller 25 stores the endoscope information read from the memory 16 in the memory 24, and then controls the light source unit 21 to switch the light sources 31a, 31b and 31c from "off" to "on", and controls the driver unit 22 to output first and second drive signals, which will be described later, from the signal generator 33.

Figure 3:
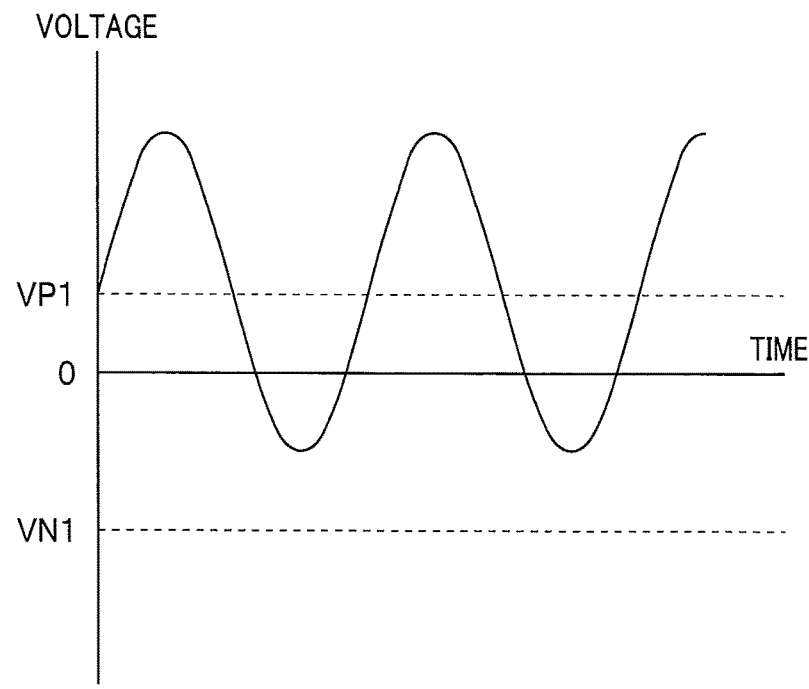
FIG. 3 is a diagram illustrating an example of a waveform of a first drive signal, which is used for driving the actuator section provided in the scanning endoscope.

Based on the control performed by the controller 25, the signal generator 33 generates a first drive signal having, for example, the waveform illustrated in FIG. 3 as a drive signal for driving the actuators 15a and 15b and outputs the first drive signal to the D/A converter 34a. FIG. 3 is a diagram illustrating an example of a waveform of the first drive signal used for driving the actuator section provided in the scanning endoscope.

More specifically, based on the control performed by the controller 25, the signal generator 33 generates, for example, a sine wave having a voltage value periodically varying with a positive voltage value VP1 that is larger than zero as a center and having an amplitude value (peak value) that does not exceed (does not fall below) a negative voltage value VN1 corresponding to a coercive electric field in each of the actuators 15a and 15b, as a first drive signal (see FIG. 3).

Figure 4:
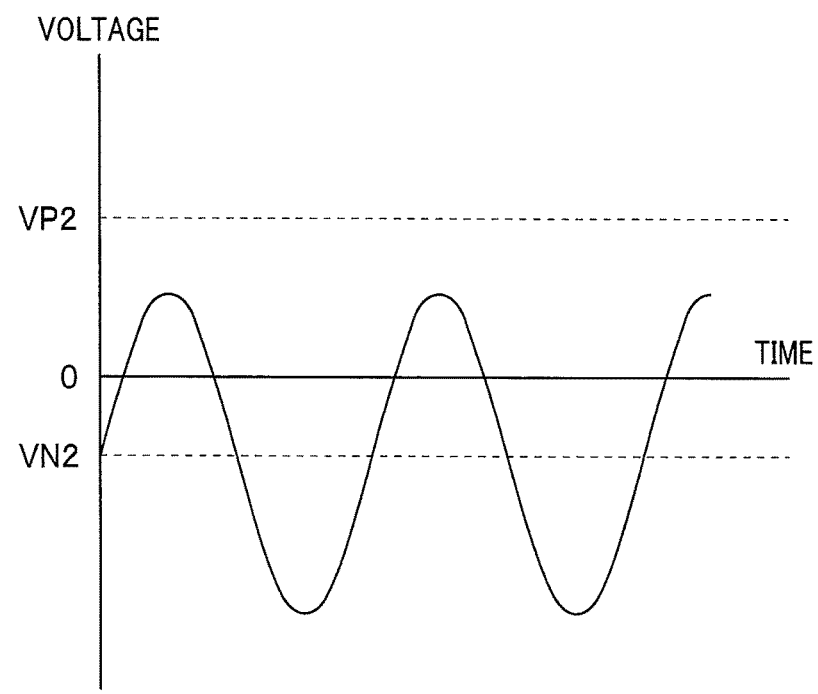
FIG. 4 is a diagram illustrating an example of a waveform of a second drive signal, which is used for driving the actuator section provided in the scanning endoscope.

Also, based on the control performed by the controller 25, the signal generator 33 generates a second drive signal having, for example, the waveform illustrated in FIG. 4 as a drive signal for driving the actuators 15c and 15d and outputs the second drive signal to the D/A converter 34b. FIG. 4 is a diagram illustrating an example of a waveform of the second drive signal used for driving the actuator section provided in the scanning endoscope.

More specifically, based on the control performed by the controller 25, the signal generator 33 generates, for example, a sine wave having a voltage value periodically varying with a negative voltage value VN2 that is smaller than zero as a center and having an amplitude value (peak value) that does not exceed (is not larger than) a positive voltage value VP2 corresponding to a coercive electric field in each of the actuators 15c and 15d, as a second drive signal (see FIG. 4).

Note that the aforementioned negative voltage value VN1 is a value determined according to a thickness in the polarization direction of the piezoelectric element in each of the actuators 15a and 15b. Also, the aforementioned positive voltage value VP2 is a value determined according to a thickness in the polarization direction of the piezoelectric element in each of the actuators 15c and 15d. Thus, for example, if the actuators 15a to 15d are formed by respective piezoelectric elements having a same thickness in the respective polarization directions, a relationship of VN1=VP2 holds between the negative voltage value VN1 and the positive voltage value VP2.

The above-described first and second drive signals are generated so as to have a same phase and provide the relationship of VP1=VN2 in order to balance among forces applied to the ferrule 41 as a result of driving of the actuators 15a to 15d.

Then, the first drive signal generated by the signal generator 33 is outputted to the actuators 15a and 15b through the D/A converter 34a and the amplifier 35. Also, the second drive signal generated by the signal generator 33 is outputted to the actuators 15c and 15d through the D/A converter 34b and the amplifier 35.

Here, where an alternating-current voltage according to the above-described first drive signal is applied to the actuator 15a, and an alternating-current voltage according to the above-described second drive signal is applied to the actuator 15c, a force applied to the ferrule 41 as a result of expansion/contraction of the actuator 15a and a force applied to the ferrule 41 as a result of expansion/contraction of the actuator 15c are cancelled out. Thus, as a result of the alternating-current voltage according to the first drive signal being applied to the actuator 15a and the alternating-current voltage according to the second drive signal being applied to the actuator 15c, the illumination fiber 12 can be swung while a position in the X-axis direction of the ferrule 41 in a case where no voltage is applied to either of the actuators 15a and 15c (where neither of the actuators 15a and 15c expands/contracts) is maintained.

Also, where the alternating-current voltage according to the first drive signal is applied to the actuator 15b and the alternating-current voltage according to the second drive signal is applied to the actuator 15d, a force applied to the ferrule 41 as a result of expansion/contraction of the actuator 15b and a force applied to the ferrule 41 as a result of expansion/contraction of the actuator 15d are cancelled out. Thus, as a result of the alternating-current voltage according to the first drive signal being applied to the actuator 15b and the alternating-current voltage according to the second drive signal being applied to the actuator 15d, the illumination fiber 12 can be swung while a position in the Y-axis direction of the ferrule 41 in a case where no voltage is applied to either of the actuators 15b and 15d (where neither of the actuators 15b and 15d expands/contracts) is maintained.

In a case where the illumination fiber 12 is swung by means of a conventional method in which, for example, an alternating-current voltage according to a drive signal whose voltage value periodically varies with a voltage value of zero as a center is applied to each of the actuators 15a to 15d, there is substantially no need to take balancing of forces applied to the ferrule 41 into account; however, in order to maintain polarization of the actuators 15a to 15d, there is a need to set an amplitude value within a range between the negative voltage value VN1 corresponding to a coercive electric field in each of the actuators 15a and 15b and the positive voltage value VP2 corresponding to a coercive electric field in each of the actuators 15c and 15d (within a range of no less than VN1 and no more than VP2).

On the other hand, according to the present embodiment, the alternating-current voltage according to the first drive signal whose voltage value periodically varies with the positive voltage value VP1 as a center is applied to the actuators 15a and 15b and the alternating-current voltage according to the second drive signal whose voltage value periodically varies with the negative voltage value VN2 as a center is applied to the actuators 15c and 15d, thereby relaxing the limitations on the amplitude value (peak value) by the negative voltage value VN1 and the positive voltage value VP2. As a result, the present embodiment enables the illumination fiber 12 to be swung in a wide area compared to the conventional method, that is, enables a scanning area of an object to be widened compared to the conventional method.

It should be understood that the present invention is not limited to the above-described embodiment, and various modifications and applications are possible without departing from the spirit of the invention.

What is claimed is:

1. A scanning endoscope system comprising:
   a fiber configured to guide illuminating light emitted from a light source;
   a first actuator disposed on a side of the fiber, wherein the first actuator is configured to deform by expanding and contracting upon application of an applied voltage, according to a first drive signal, thereby swinging the fiber;
   a second actuator disposed at a position facing the first actuator across the fiber, wherein the second actuator is configured to deform by expanding and contracting upon application of according to an applied voltage, according to a second drive signal, thereby swinging the fiber;
   a drive signal output section configured to output the first drive signal and the second drive signal, wherein the first actuator and the second actuator are configured to deform in opposite directions when a polarity of the first drive signal and a polarity of the second drive signal are the same; and
   a controller configured to control the drive signal output section to:
      generate the first drive signal varying with a first voltage as a center, and set the first voltage greater than zero,
      generate the second drive signal varying with a second voltage as a center, and set the second voltage less than zero, and
      align a phase of the first drive signal and the second drive signal.

2. The scanning endoscope system according to claim 1, wherein the first actuator comprises a first piezoelectric element, wherein the first piezoelectric element is configured to contract when the polarity of the first drive signal is positive and to expand when the polarity of the first drive signal is negative; and
   wherein the second actuator comprises a second piezoelectric element, wherein the second piezoelectric element is configured to contract when the polarity of the second drive signal is negative and to expand when the polarity of the second drive signal is positive.

3. The scanning endoscope system according to claim 1, wherein each of the first actuator and the second actuator comprises a piezoelectric element,
   wherein the controller is configured to control the drive signal output section to generate the first drive signal such that an amplitude value of the first drive signal is set so as not to exceed a voltage value corresponding to a coercive electric field in the piezoelectric element of the first actuator, and
   wherein the controller is configured to control the drive signal output section to generate the second drive signal such that an amplitude value of the second drive signal is set so as not to exceed a voltage value corresponding to a coercive electric field in the piezoelectric element of the second actuator.

4. The scanning endoscope system according to claim 3, wherein the respective piezoelectric elements comprising the first actuator and the second actuator are subjected to polarization processing in advance so as to have a same polarization direction along a predetermined axis direction and formed so as to have a same thickness in the polarization direction.

5. The scanning endoscope system according to claim 1, wherein the controller is configured to control the drive signal output section to generate the first drive signal and the second drive signal such that a voltage value of the first drive signal is equal to a voltage value of the second drive signal, if the polarity of the first drive signal is reversed.

6. The scanning endoscope system according to claim 1 further comprising:
   a light-receiving section configured to receive from an object illuminated by the illuminating light;

a light-detecting section configured to generate a signal according to an intensity of the light received by the light-receiving section and output the signal; and an image-generating section configured to generate an image of the object based on the signal outputted from the light-detecting section.

\* \* \* \* \*

UNITED STATES PATENT AND TRADEMARK OFFICE
CERTIFICATE OF CORRECTION

PATENT NO. : 9,629,517 B2
APPLICATION NO. : 14/269297
DATED : April 25, 2017
INVENTOR(S) : Yuji Sakai et al.

Page 1 of 1

It is certified that error appears in the above-identified patent and that said Letters Patent is hereby corrected as shown below:

Column 7, Claim 1, Line 5 should read:
first actuator is configured to deform by expanding or Column 8, Claim 6, Line 3 should read:
a light-receiving section configured to receive light from an Signed and Sealed this
Twelfth Day of September, 2017

Joseph Matal
*Performing the Functions and Duties of the*
*Under Secretary of Commerce for Intellectual Property and*
*Director of the United States Patent and Trademark Office*